United States Patent [19]

Kelman et al.

[11] Patent Number: 5,104,957
[45] Date of Patent: Apr. 14, 1992

[54] BIOLOGICALLY COMPATIBLE COLLAGENOUS REACTION PRODUCT AND ARTICLES USEFUL AS MEDICAL IMPLANTS PRODUCED THEREFROM

[75] Inventors: Charles D. Kelman, New York, N.Y.; Dale P. DeVore, Chelmsford, Mass.

[73] Assignee: Autogenesis Technologies, Inc., Acton, Mass.

[21] Appl. No.: 486,558

[22] Filed: Feb. 28, 1990

[51] Int. Cl.$^5$ ............................................. C08H 1/06
[52] U.S. Cl. ............................................... 527/201
[58] Field of Search .................................. 527/201

[56] References Cited

U.S. PATENT DOCUMENTS

| | | | |
|---|---|---|---|
| 2,948,706 | 8/1960 | Schellenberg et al. | 525/56 |
| 3,453,222 | 7/1969 | Young | 534/8 |
| 3,949,073 | 4/1976 | Daniels et al. | 514/2 |
| 4,021,245 | 5/1977 | Nagatoma et al. | 430/537 |
| 4,215,200 | 7/1980 | Miyata et al. | 475/273 |
| 4,223,984 | 9/1980 | Miyata et al. | 264/1.1 |
| 4,233,360 | 11/1980 | Luck et al. | 530/354 |
| 4,260,228 | 4/1981 | Miyata | 527/201 |
| 4,264,155 | 4/1981 | Miyata | 351/160 H |
| 4,264,493 | 4/1981 | Battista | 530/354 |
| 4,268,131 | 5/1981 | Miyata et al. | 435/273 |
| 4,349,470 | 9/1982 | Battista | 530/354 |
| 4,388,428 | 6/1983 | Kuzma et al. | 523/106 |
| 4,424,208 | 1/1984 | Miyata et al. | 514/21 |
| 4,427,808 | 1/1984 | Stol et al. | 524/24 |
| 4,452,925 | 6/1984 | Kuzma et al. | 523/106 |
| 4,488,911 | 12/1984 | Luck et al. | 106/161 |
| 4,563,490 | 1/1986 | Stol et al. | 524/24 |
| 4,572,832 | 2/1986 | Kigasawa et al. | 424/435 |
| 4,581,030 | 4/1986 | Bruns et al. | 623/5 |
| 4,650,616 | 3/1987 | Wajs | 264/2.6 |
| 4,687,518 | 8/1987 | Miyata et al. | 106/161 |

FOREIGN PATENT DOCUMENTS 1-297484 11/1989 Japan.
WO83/00339 2/1983 PCT Int'l Appl..
AU87/00001 7/1987 PCT Int'l Appl..

OTHER PUBLICATIONS

Chvapil and Krajicek, *J. Surg. Research*, vol. 3(7): 358, 1963.
Dunn et al., *Science*, 157: 1329, 1967.
Nishihara et al., *Trans. Amer. Soc. Artif. Int. Organs*, vol. XIII, pp. 243–248, 1967.
Studies on Copolymer of Collagen and a Synthetic Polymer, Y. Shimizu et al., Biomat., Med. Dev., Art. Org., 5(1), pp. 49–66 (1977).
Studies on Composites of Collagen and a Synthetic Polymer, Y. Shimizu et al., Biomat., Med. Dev., Art. Org., 6(4), pp. 375–391 (1978).
Biomedical and Dental Applications of Polymers, Charles G. Gebelein et al., Polymer Science and Technology, vol. 14, Plenum Press, Re: Covalent Bonding of Collagen and Acrylic Polymers by Douglas R. Lloyd et al., pp. 59–84, 1980.
Chemical Abstracts, vol. 110(17), 1989, Abstract No. 154899.
Civerchia-Perez, L. et al., *Proc. Natl. Acad. Sci. USA*, 77(4): 2064–68 (1980) "SMA Resins: The Multifunctional Resins," Arco Chemical Company, General Bulletin.

*Primary Examiner*—Nathan M. Nutter
*Assistant Examiner*—Jeffrey Culpeper Mullis
*Attorney, Agent, or Firm*—Darby & Darby

[57] ABSTRACT

The present invention provides a biologically compatible collagenous reaction product comprising ethylenically unsaturated or polymeric substituted collagen, the monomeric substituents being essentially free of nitrogen, e.g., methacrylate styrene, polyvinyl, ethylene. The collagenous reaction product can be polymerized, e.g., by exposure to UV irradiation, chemical agents or atmospheric oxygen, and molded to form useful medical implant articles. Methods of preparation are also provided.

23 Claims, 1 Drawing Sheet

FIG. 1A
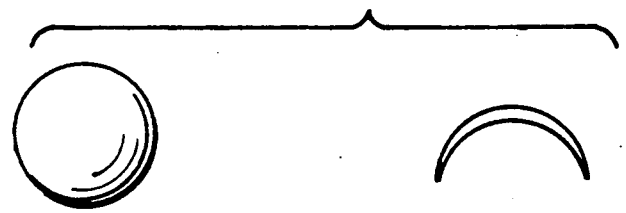
FIG. 1B    FIG. 1C
    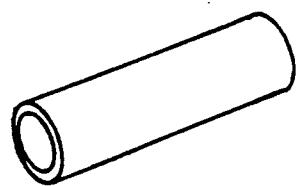
FIG. 1D    FIG. 1E
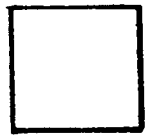    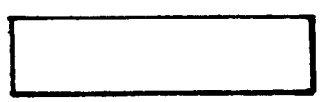

BIOLOGICALLY COMPATIBLE COLLAGENOUS REACTION PRODUCT AND ARTICLES USEFUL AS MEDICAL IMPLANTS PRODUCED THEREFROM

FIELD AND BACKGROUND OF THE INVENTION

The present invention relates to a biologically compatible collagenous reaction product comprising ethylenically unsaturated or polymers substituted collagen. More particularly, the invention relates to a collagenous reaction product that can be polymerized to form shaped articles useful in medical applications, including implants for ophthalmology, surgery, orthopedics and cardiology.

Various methods and materials have been proposed for modifying collagen to render it more suitable for biological and medical procedures. (See, e.g., Lloyd et al., "Covalent Bonding of Collagen and Acrylic Polymers," *American Chemical Society Symposium on Biomedical and Dental Applications of Polymers,* Polymer Science and Technology, Vol. 14, Plenum Press (Gebelein and Koblitz, eds.), New York, 1980, pp. 59–84; Shimizu et al., *Biomat. Med. Dev. Art. Org.,* 5(1):49–66 (1977); and Shimizu et al., *Biomat. Med. Dev. Art. Org.,* 6(4):375–391 (1978), for general discussion on collagen and synthetic polymers.)

In U.S. Pat. Nos. 4,427,808 and 4,563,490, Stol et al. disclose composite polymeric materials and methods for preparing such materials. The polymeric materials consist of a hydrophilic polymer or copolymer based on methacrylic or acrylic esters, fibrillar collagen and a crosslinking agent. The polymeric materials are not reacted with the fibrillar collagen. Rather, the collagen is dispersed unreacted in the hydrophilic polymer, the latter forming a matrix that is penetrated by the collagen.

In U.S. Pat. No. 3,453,222, Young discloses methods of chemically modifying proteinaceous materials, e.g., collagen, by reaction under mild alkaline conditions with alkane and alkene sultones, e.g., 3-hydroxy-1-propene sulfonic acid sultone. Young's disclosed sultone modified protein products and methods are not useful in biological and medical procedures due to their low biocompatibility.

In U.S. Pat. Nos. 4,388,428 and 4,452,925, Kuzma et al. disclose polymerized hydrophilic water-swellable compositions made from a mixture of components consisting essentially of inter alia solubilized collagen and ethylenically unsaturated monomers containing nitrogen. (See also PCT Int. Appl. No. PCT/US82/00889, published Feb. 3, 1983 as WO 83/00339). A severe drawback to Kuzma et al.'s compositions which limits their usefulness as biological materials is the presence of significant quantities of acrylamides, known neurotoxins, as ethylenically unsaturated monomers. No recognition of the neurotoxicity of acrylamides is made in any of these patent.

Miyata et al., U.S. Pat. No. 4,215,200, describes chemically modified polymeric collagen hemostatic agents in powder and gel forms. The specific polymeric collagen is said to assume regularly staggered quaternary structure and a high positive electrostatic charge at physiological pH, i.e., about 7.4, when guanidinated, esterified, and/or esterified-guanidinated. No mention or suggestion is made in the '200 patent as to acylating collagen to obtain collagenous materials with plastic-like properties.

In other developments, U.S. Pat. No. 4,264,155 (issued to Miyata) discloses soft contact lenses made from collagen gels to which water-soluble organic polyhydroxy polymers, e.g., mucopolysaccharides, polyvinyl alcohols and the like are added, followed by chemical crosslinking of the gels. The polyhydroxy polymeric additives are said to "surround" the strands of the collagen molecules to protect them against microbial degradation. No teaching or suggestion is made in U.S. Pat. No. 4,264,155 of possibly acylating collagen to produce ethylenically unsaturated or polymers substituted collagen which could then be polymerized to form useful biomedical articles having high biological and tissue acceptability.

SUMMARY OF THE INVENTION

The present inventors have discovered that a biologically compatible collagenous reaction product can be formed by reacting collagen, e.g., purified Type I collagen, with acylating agents such as ethylene/maleic anhydride copolymer, styrene/maleic anhydride copolymer, poly(vinyl) sulfonic acid and similar acid chlorides, sulfonic acid, sulfonyl chlorides and anhydrides. The resulting acylated collagenous reaction product comprises unsaturated or polymers substituted collagen with plastic-like properties. The substituents in the collagenous reaction product of the present invention are essentially free of nitrogen, and thus do not contain acrylamides or other neurotoxins containing nitrogen which would limit their usefulness in biological and medical applications, in contrast to the prior art.

The present inventor has also discovered that the collagenous reaction product can be polymerized to form articles, including shaped articles, useful as medical implant and transplant articles, e.g., ophthalmic lenses including contact lenses, corneal onlays and inlays and intraocular lens (IOLs). Other useful articles for implantation include synthetic blood vessels and molded soft tissue implants for surgery.

BRIEF DESCRIPTION OF THE FIGURES

FIG. 1 illustrates various collagen-based implants.
FIG. 1A illustrates a contact lens;
FIG. 1B illustrates a substituent lens;
FIG. 1C illustrates a tubular device;
FIG. 1D illustrates a tympanic membrane replacement; and
FIG. 1E illustrates a film.

DETAILED DESCRIPTION OF THE INVENTION

All patents, publications and literature references are incorporated by reference in their entirety.

The present invention provides a biologically compatible collagenous reaction product with plastic properties which are provided by incorporating ethylenically unsaturated or polymeric substituents into collagen. The substituents are incorporated by reacting suitable collagen with an acylating agent containing ethene moieties or acylating agents which are polymers.

As employed herein, the term "biologically compatible" refers to collagen modified in accordance with the present invention (i.e., a collagenous reaction product) which is stable when incorporated or implanted into or placed adjacent to the biological tissue of a subject and more particularly, does not deteriorate appreciably over time or induce an immune response or deleterious tissue reaction after such incorporation or implantation or placement.

The type of collagen useful to form the biologically compatible collagenous reaction product of this invention is selected from the following groups: purified Type I collagen, Type IV collagen and Type III collagen, intact collagen-rich tissue, or a combination of any of the foregoing. Preferred as a collagen starting material is purified Type I collagen. Type I collagen is widely available and extracted from animal sources, e.g., mammalian tissues, including human (dermis) and bovine (cow hide).

The substituents are ethylenically unsaturated or polymeric and essentially free of nitrogen, such as the nitrogen found in acrylamides which are known to be neurotoxins. This feature of the substituents allows them to be safely employed in collagen-based compositions for use as biomedical materials for implantation, surgery and the like.

The substituents useful in the practice of this invention comprise the following: methacrylate, styrene, polyvinyl and ethylene.

It has been discovered that these substituents are chemically incorporated into collagen when an effective amount of an acylating agent is allowed to react with collagen or a collagenous preparation. Suitable acylating agents include by way of non-limiting example, methacrylic anhydride, styrene/maleic anhydride copolymer, polyvinyl sulfonic acid, ethylene/maleic anhydride copolymer, B-styrene sulfonyl chloride, each of which is available from Aldrich Company (Milwaukee, Wisc.).

The present invention accordingly provides a number of collagenous reaction products, that is, a polymerized biologically compatible collagenous reaction product useful to form medical implant articles. This polymerized reaction product comprises ethylenically unsaturated substituted collagen and polymers substituted collagen, the substituents being essentially free of nitrogen. By way of illustration only, methacrylic anhydride and collagen can be reacted to form collagen methacrylate followed by polymerization in the presence of oxygen or UV irradiation to make polycollagen methacrylate. Similarly, collagen can be reacted with the following acylating agents: styrene/maleic anhydride copolymer, polyvinyl sulfonic acid and ethylene/maleic anhydride copolymer to form collagen styrene, collagen polyvinyl and collagen ethylene compositions, respectively. After polymerization, the collagen styrene, collagen polyvinyl and collagen ethylene compositions will form polycollagen styrene, polycollagen ethylene and polycollagen polyvinyl polymers, respectively.

An effective amount of the acylating agent will vary within limits but generally comprises from about 0.5 to about 20 weight percent total collagen, preferably from about 5 to about 10 weight percent total collagen in solution. The effective amount of the acylating agent will be based on the total amount of collagen in the solution.

Acylation of the collagen is carried out at alkaline pH, for example, in the range of from about 8.0 to about 10.0 pH, preferably at about pH 9.0 or so. In order to achieve complete acylation of the collagen that is being treated, which is desirable because it leads to better performance in the final shaped implant articles (i.e., the properties of the incorporated monomers are better imparted to the final articles), the collagen should be filtered and solubilized. Using conventional filtering means, e.g., a millipore filter with a 3 um pore size, the collagen can be filtered to remove impurities and contaminants. The filtered collagen can then be solubilized (i.e., dissolved or dispersed) in a suitable proteolytic solution, e.g., pepsin.

It has also been found that the reaction between the collagen and the acylating agent may require more than one reaction "run." That is, additional acylating agent can be added to the initial reaction mixture (i.e., the initial collagen and the initial acylating agent) to continue the reaction to completion, i.e., complete acylation of the collagen being treated.

The reaction time for the acylation of the collagen will vary according to a number of factors including the amount of collagen to be acylated, the type of acylating agent, the pH and temperature of the reaction mixture, to name just a few factors. In addition, the method of addition of the acylating agent to the suitable collagen will affect the reaction time. For example, addition of the acylating agent as a solid or in an appropriate solution will increase and decrease the reaction time, respectively. Reaction time is generally slower if the acylating agents are added as solids or powders.

In general, the acylation reaction should proceed to completion within a time ranging from about 5 to about 90 minutes, preferably from about 20 to about 40 minutes. The acylation reaction should generally be carried out at a temperature of from about 4° to about 37° C., preferably from about 4° to 25° C.

The acylation reaction can be monitored by the decrease in pH. The reaction is complete when pH is stable at 9.0. The reaction can also be monitored by removing aliquots and measuring the free amine concentration of precipitated, washed collagen product.

The reaction can be stopped by adjusting the pH to 12.0 for 2 minutes which destroys the acylating agents. The modified collagen is then precipitated by reducing the pH using hydrochloric acid, acetic acid, nitric acid, sulfuric acid, or other acid.

The amount of acid added should be sufficient to cause the pH of the reaction mixture to fall to below pH 5.0, preferably from about pH 4.0 to about 4.5 or so. When the acid is added to the mixture, and it is suggested that the addition be in small quantities, e.g., dropwise, the mixture should become cloudy indicating a change to acidic pH of the collagen mixture as the modified or reacted collagen "falls out of solution."

A precipitate of the reacted collagen which now contains ethylenically unsaturated or polymeric substituent groups can be recovered from the cloudy (acidic) reaction mixture using conventional recovery techniques, e.g., centrifugation at 4,000 to 15,000 RPM for about 10–60 minutes, preferably centrifugation at about 6,000 to about 12,000 RPM for about 20 to about 30 minutes.

After recovery, the precipitate can be washed with deionized water and subsequently dissolved in a physiological solution, e.g., phosphate buffer (0.1 M) at pH 6.8 or so. In order to dissolve the washed precipitate well, it may be necessary to adjust the pH from about 6.5 to about 7.4 by addition of sodium hydroxide. (Sodium bicarbonate may also be used to adjust pH. However, it probably does not specifically act to solubilize monomers.)

Following the dissolution of the precipitate in solution, the suspension can be centrifugated to remove air bubbles present in the suspension. At this point, the resulting fluid should assume a viscous consistency and slightly cloudy appearance.

The fluid thus obtained can be subsequently subjected to polymerizing or crosslinking conditions. Polymerization can be carried out using UV irradiation, e.g., UV irradiation or gamma irradiation in the absence of oxygen. UV polymerization may be accomplished using a short wavelength UV source (254 nm) from about 4–16 watts and an exposure time of from about 10 to about 40 minutes, in the absence of oxygen. Preferably, polymerization is accomplished by exposure to an 8 watt, short wavelength source for about 20–30 minutes at a distance of from 4 cm. to about 10 cm. Polymerization using gamma irradiation has been done using from 0.5–2.5 MRads. Excess UV irradiation will depolymerize collagen polymers. Gamma irradiation has also been shown to degrade collagen.

In addition, polymerization can be effected using chemical agents, e.g., glutaraldehyde, formaldehyde, isocyanates, epoxy compounds, bifunctional acylating agents, or a combination of any of the foregoing.

Preferred as a polymerizing agent is UV irradiation. It should also be pointed out that polymerization or crosslinking of the substituted collagen can be carried out by simply exposing the material to atmospheric oxygen, although the rate of polymerization is appreciably slower than in the case of UV irradiation or chemical agents. Polymerization can also be done in steps. For example, collagen solutions can be placed in molds, exposed to UV-irradiation, dehydrated in a laminar-flow hood, and again exposed to UV irradiation.

The polymerized materials can assume a number of sizes and shapes consistent with their intended biomedical applications, which include use in ophthalmology, plastic surgery, orthopedics and cardiology.

For example, hydrogels, e.g., polymethylmethacrylate, are currently used as biomedical materials having physical properties similar to human tissue. By including an appropriate collagen backbone in a hydrogel composition, the biological or tissue compatibility will be enhanced while at the same time maintaining useful plastic properties, such as flexibility, moldability, elasticity, strength and transparency, to name just a few.

Thus, collagen based polymers, including collagen-based hydrogels in accordance with the present invention, are useful to make ophthalmic lens devices, such as contact lens, corneal onlays and inlays, and IOLs. Methods for making such ophthalmic lens devices are well-known in the art. For example, Miyata, U.S. Pat. Nos. 4,260,228 and 4,264,155; Miyata et al., U.S. Pat. Nos. 4,223,984, 4,268,131 and 4,687,518; Wajs, U.S. Pat. No. 4,650,616; and Kuzma et al., U.S. Pat. No. 4,452,925, describe a methods for constructing contact lenses. Burns et al., U.S. Pat. No. 4,581,030, and Battista, U.S. Pat. No. 4,264,493 describe methods for making IOLs. Such devices exhibit useful characteristics including high water content, high refractive index and high permeability to oxygen and nutrients. Styrene and methacrylate derivatives, e.g., polycollagen styrene and polycollagen methacrylate, exhibit a very high refraction index. Styrene has an $N_D^{25}$ of about 1.60 and methacrylate has an $N_D^{25}$ of about 1.43143.

Other collagen-based polymers, such as polyethylene collagen and polystyrene collagen, can be molded or fabricated to form synthetic blood vessels or soft tissue implants for plastic surgery using techniques known in the art. For example, Huc and Gimeno, French patent application No. 84/3181, 1984, and Chvapil and Krajicek, *J. Surg. Research*, 11: 358, 1963, describe methods for forming synthetic blood vessels. Daniels et al., U.S. Pat. No. 3,949,073, and Wallace et al., U.S. Pat. No. 4,424,208, disclose the preparation of soft tissue implants. A synthetic tympanic membrane is disclosed by Abbenhaus and Hemenway, *Surg. Forum*, 18: 490, 1967. The preparation of other collagen-based membranes and films is disclosed by Dunn et al., *Science*, 157: 1329, 1967, and Nishihara et al., *Trans. Amer. Soc. Artif. Int. Organs.* Vol. XIII, pp. 243–248, 1967. A number of other collagen-based prostheses are disclosed by Luck et al., U.S. Pat. Nos. 4,233,360 and 4,488,911, and Battista, U.S. Pat. No. 4,349,470. Additional uses of collagen-based implants are reviewed by Simpson in "Collagen as a Biomaterial," *Biomaterial in Reconstructive Surgery*, C. V. Mosby Co. (L. Rubin, ed.), St. Louis, 1983, pp. 109–117.

Furthermore, the polymerized materials, i.e., polymerized collagenous reaction products, can be made in the form of a film, particularly in the case of polymethylmethacrylate monomers. As described in the examples which follow, such a film is flexible and elastic with the consistency and feel of plastic film, and yet the film exhibits high biological compatibility. Uses of such films include: Prevention of adhesion formation following tendon surgery (i.e., use as a wrap around tendons), use as a synthetic tympanic membrane, substitute facial tissue and wound dressing component. Solutions of ethylenically unsaturated substituted collagen could be useful as vitreous replacements, viscoelastic solutions for ophthalmic surgery, joint lubricants, etc.

Intact collagen-rich tissue having a naturally acquired useful shape, such as human umbilical veins, can also be acylated and polymerized according to the present invention. Such articles should be biologically compatible and have useful plastic-like properties including elasticity, strength and flexibility.

The present invention provides a method of preparing a biologically compatible collagenous reaction product comprising ethylenically unsaturated or polymeric-substituted collagen in which the substituents are essentially free of nitrogen. This method comprises the steps of: contacting solubilized collagen with an effective amount of an acylating agent comprising ethene or polymeric moieties under suitable conditions to form a precipitate and recovering the formed precipitate.

The present invention further provides a method of preparing a shaped article useful for medical implantation in which the article comprises a polymerized biologically compatible collagenous reaction product comprising ethylenically unsaturated or polymeric substituted collagen. These substituents are essentially free of nitrogen. This method comprises the steps of: forming a precipitate by contacting solubilized collagen with an effective amount of an ethylenically or polymeric substituted acylating agent under suitable conditions; recovering the formed precipitate; suspending the recovered precipitate in a solution; and polymerizing the suspension in a mold, to prepare a shaped article useful for medical implantation thereby. The type of collagen, acylating agent, effective amount and means for precipitating and recovering the formed precipitate are as described above, in the examples which follow, or are conventionally known in the art.

The following examples are set forth by way of illustration and not limitation of the present invention.

PREPARATION OF TYPE I COLLAGEN (BOVINE HIDE)

A. Fibrous Type I collagen was prepared from bovine material (calf hide) using the following procedure:

1. Clean, dehaired split hides, which are commercially available from the Andre Manufacturing Co., Newark, N.J., and stored frozen in sealed plastic bags until ready to use.

2. Thaw approximately 200 g of cow hide at room temperature.

3. Cut the hide into small pieces, approximately 1 $cm^3$ using a scalpel and tweezers. Weigh the wet tissue and record its weight.

4. Place the cow hide in 15 liters of 0.5 M acetic acid and stir at room temperature using a lightning mixer for at least one hour. The cow hide will swell.

5. Add 2% or 3.9 g of pepsin from porcine stomach mucosa (manufactured by Sigma Chemicals, St. Louis, Mo.) to the cow hide solution, after dissolving it in approximately 10 mls of 0.5 M acetic acid. Continue stirring with mixer overnight.

6. Add 1% or 1.96 g of the above pepsin to the cow hide solution dissolved in approximately 10 mls of 0.5 M acetic acid. Continue stirring with mixer overnight.

7. Refrigerate the dissolved cow hide solution until it is uniformly at a temperature of about 4° C. This may take until overnight.

8. Remove the solution from the cooler and begin stirring with the lightning mixer. Increase the pH of the solution to 9.0 using 10N NaOH to denature the pepsin. Ice cubes may be added during the process to keep the solution cold. (Collagen will precipitate at pH 9.0 if the temperature is higher than 6° C.) Quickly return the solution to 4° C. The solution must remain in the cooler for at least 4 hours.

9. Remove the solution from the cooler and centrifuge at 4° C. for 30 minutes at 9 rpm. Save the supernatant, which contains the collagen and discard the precipitate, which contains the pepsin.

10. Add enough NaCl to the solution to bring up the concentration to 2.5 M. This will precipitate the desired collagen. Stir with the lightning mixer for at least two hours.

11. Centrifuge for 30 minutes at 9 rpm to recover precipitate. The resultant collagen precipitate is collected and then reconstituted in 15 liters of 0.5 M acetic acid (at least two hours).

12. The collagen solution is precipitated again by adding enough NaCl to the solution to bring up the concentration to 0.8 M. It is stirred well for at least two hours then centrifuged for 30 minutes at 9 rpm.

13. The precipitate is collected and then reconstituted in 15 liters of 0.5 M acetic acid (at least two hours).

14. Enough NaCl is added to the collagen solution to bring up the concentration to 0.8 M. The precipitate is formed by mixing for at least two hours. Centrifugation at 9 rpm for 30 minutes will recover the precipitate.

15. For the final time the precipitate is collected and then reconstituted in 0.1 M acetic acid to provide a high purity of approximately 0.3 percent wt/wt collagen Type I solution having a pH of about 3.

16. The collagen solution is filtered first through a prefilter which has a pore size of about 0.3 um and then through a final filter which has a pore size of 0.22 um for sterilization. This material can now be used in the modification procedure to prepare collagenous reaction products in accordance with this invention and as described in further detail in the examples hereinbelow.

EXAMPLE 1

Preparation of Methacrylate Substituted Collagenous Reaction Product

One hundred milliliters of 3 u filtered, pepsin-solubilized collagen prepared above was reacted with 10 drops of methacrylic anhydride in 10 drops of anhydrous alcohol at pH 9.0. The pH was maintained at pH 9.0 during the reaction. A second addition of 5 drops of methacrylic anhydride in 5 drops of alcohol was made to continue the acylation reaction. After forty minutes of reaction, the pH was lowered to 4.3 by the addition of 1N HCl. The mixture became cloudy and was centrifuged at 12,000 RPM for twenty minutes. The precipitate was dissolved in 0.1 M phosphate buffer, pH 6.8. However, because the precipitate did not dissolve well, several drops of 5% sodium bicarbonate were added. (Note: methacrylate monomers are soluble in 5% bicarbonate). The precipitate thus dissolved and the suspension was centrifuged to remove air bubbles. The resulting fluid was viscous and slightly cloudy. An aliquot was placed on a glass slide and exposed to UV irradiation for twenty minutes. The polymerized film was clear and had the properties of a flexible plastic. It was also observed that the collagen methacrylate spontaneously polymerized over time, probably due to exposure to oxygen.

EXAMPLE 1A

Methacrylic Substituted Collagen Reaction Product Preparation

A second procedure for forming methacrylic substituted collagen reaction products was conducted as follows: one hundred milliliters of 0.45 um filtered, pepsin solubilized bovine collagen was reacted with 5 drops of methacrylic anhydride. The collagen solution was first brought to pH 9.0 by addition of 10N and 1N sodium hydroxide. The pH was maintained at pH 9.0 during the reaction by addition of 1N sodium hydroxide. After 30 minutes, the pH was dropped to 4.3 by addition of 6N and 1N hydrochloric acid. The precipitate was recovered by centrifugation at 8,000 rpm and washed three times with sterile water. The washed precipitate was then dissolved in 0.05N phosphate buffer. Sodium hydroxide was added to bring the pH to about 7.2. The solution was centrifuged at 8,000 rpm to remove bubbles introduced during mixing. The solution was slightly cloudy. Films were cast in molds and air polymerized or polymerized using UV-irradiation. Polymerized films had physical properties similar to plastics. Methacrylic substituted collagen appeared to polymerize without external catalysts. The polymerization was accelerated using UV-irradiation in a nitrogen environment. Accelerated polymerization was also accomplished by adding 5-20 milligrams of sodium persulfate per milliliter of substituted collagen and exposing this mixture to UV-irradiation. In this case polymerization occurred rapidly in air. Removal of oxygen was not necessary.

EXAMPLE 1B

Preparation of Methacrylic/Glutaric Substituted Collagen

The procedure described above was repeated except that glutaric anhydride was added along with methacrylic anhydride. One hundred milliliters of collagen solution were brought to pH 9.0. Twenty milligrams of glutaric anhydride in 0.5 milliliters of dimethyl formamide were added to the solution and the pH maintained at 9.0. After approximately 2 minutes, 3 drops of methacrylic anhydride were added and the pH maintained at pH 9.0. The reaction continued for 35 minutes, after which the reaction product was recovered as described in Example 1A. The modified collagen was dissolved in buffer and centrifuged. The solution was clear and subsequent films were clearer than observed in Example 1A.

EXAMPLE 1C

Preparation of Methacrylic/Glutaric Substituted Collagen

The procedure in Example 1B was repeated except that an additional 20 milligrams of glutaric anhydride was added following methacrylic anhydride addition. The reaction product dissolved in buffer appeared to be clear and colorless.

EXAMPLE 1D

Preparation of Methacrylic/Glutaric/Vinyl Substituted Collagen

The procedure in Example 1B was repeated except that the collagen solution was reacted with a mixture of 20 milligrams of glutaric anhydride, 5 milligrams of B-sytrene sulfonyl chloride, and 3 drops of methacrylic anhydride all in 0.5 milliliters of DMF. The mixture was added dropwise and the pH maintained at 9.0. After 30 minutes, the reaction product was recovered and dissolved in buffer. The pH was adjusted to 7.4 by addition of 1N sodium hydroxide. The solution was clear and viscous. Films were made as described previously. The polymerized films were clear and appeared stronger than films without styrene.

EXAMPLE 2

Preparation of Styrene Substituted Collagen

The procedure of Example 1B was followed except that styrene/maleic anhydride copolymer, molecular weight 350,000 was used instead of methacrylic anhydride. The reaction product was recovered by centrifugation and dissolved in buffer at pH 7.4. The solution was slightly cloudy.

EXAMPLE 2A

Preparation of Styrene/Glutaric Substituted Collagen

The procedure of Example 2 was followed except that glutaric anhydride was added before reaction with styrene-maleic anhydride copolymer. The inclusion of glutaric resulted in a solution that was clear, colorless, and viscous. Films were also clear.

EXAMPLE 2B

Preparation of Styrene/Glutaric Substituted Collagen

The procedure of Example 1A was followed except that B-styrene sulfonyl chloride was used in place of styrene/maleic anhydride copolymer. The reaction appeared to produce a substituted collagen with better "plastic" properties than previous reactions with styrene/maleic anhydride copolymer. (These products exhibited properties more like glutaric reaction products.) Films prepared from the styrene/glutaric substituted collagen were clear, colorless and strong. Evaluations of resistance to degradation by bacterial collagenase indicated that the styrene/glutaric films were 600% more resistant than films composed of only glutaric substituted collagen.

EXAMPLE 3

Preparation of Polyvinyl Substituted Collagen

The procedure of Example 1B was followed except that polyvinyl sulfonic acid was used in place of methacrylic anhydride. One hundred milliliters of soluble, bovine collagen at approximately 0.25% was brought to pH 9.0. Twenty-five milligrams of polyvinyl sulfonic acid solution was added to the collagen solution while maintaining the pH at 9.0. There was a minimal decrease in the pH. After approximately 60 minutes, the substituted collagen was recovered by reducing the pH. A small amount of precipitate formed at about pH 5.0. There was recovered and washed. Reconstitution of buffer at pH 7.3 produced a cloudy, thick dispersion. Films were made which were slightly cloudy. When these films were placed in water or buffer, they swelled to many times their original size.

EXAMPLE 3A

Preparation of Vinyl/Glutaric Substituted Collagen

The procedure followed in Example 3 was repeated except that 25 milligrams of glutaric anhydride in DMF was added first to the soluble collagen at pH 9.0. After about 10 minutes, 25 milligrams of polyvinyl sulfonic acid was added. The reaction continued for 30 additional minutes, while maintaining the pH at 9.0. The solution was clear. The reaction product(s) was precipitated at pH 4.3 and washed three times with sterile water at pH 4.3. The precipitate was then reconstituted in physiological saline (0.9%) or in phosphate buffer. The pH was adjusted to pH 7.2. The solution was clear, colorless and viscous. Films were prepared by placing aliquots of the substituted collagen in glass molds and exposing the material to UV-irradiation in nitrogen. Resultant films were clear and colorless and when placed in physiological solution or water swelled to many times their original size. If the substituted collagen solution was first heated in the molds to about 38° C., dried, and then exposed to UV-irradiation, resultant films exhibited greater elasticity and strength and did not swell to the extent noted in films prepared without heating and drying. Overall, vinyl substituted collagen films exhibit unusual swelling.

EXAMPLE 4

Preparation of Polyethylene Substituted Collagen

The procedure described in Example 1B was followed except that soluble collagen was reacted with ethylene/maleic anhydride copolymer. One hundred milliliters of soluble, bovine collagen at 0.25% was brought to pH 9.0. Approximately 25 milligrams of ethylene/maleic anhydride copolymer in DMF were added and the pH maintained at 9.0. The solution became cloudy as the reaction continued and pH decrease was slow. After about 45 minutes, the pH was reduced to about 4.3 to precipitate the substituted collagen. There was minimal precipitate which was washed and reconstituted in buffer brought to pH 7.4. The dispersion was slightly cloudy and viscous. Films prepared as described above were also cloudy. However, the films exhibited properties of plastic films.

EXAMPLE 4A

Preparation of Ethylene/Glutaric Substituted Collagen

Procedures were as in Example 4 except that the collagen solution was first treated with 25 milligrams of glutaric anhydride for 10 minutes before adding the ethylene/maleic anhydride copolymer. In some cases an additional amount of glutaric anhydride was added following ethylene/maleic anhydride copolymer. pH was maintained 9.0 throughout the reaction. The reaction product was recovered by precipitation at about 4.3. This was washed and reconstituted in saline (0.9%) or phosphate buffer at pH 7.2. Additional sodium hydroxide was added to bring the pH to 7.2. The solutions were colorless, viscous and just slightly cloudy. Films were prepared by drying and then UV-irradiation, by UV-irradiation without prior drying, and by heating, drying and UV-irradiation. Unlike glutaric preparations that melted (became fluid) at 34°-38° C., these ethylene/glutaric preparations were stable at 50° C. Films also exhibited enhanced stability as determined by rates of dissolution in physiological solution. Thus ethylene appears to impart enhanced stability to films prepared with substituted collagens. Ethylene films appeared stronger than other films prepared from substituted collagens.

EXAMPLE 5

Combination Substitutions

Procedures described in the previous Examples were used to prepare several combination substitutions. Combinations of reaction agents included: glutaric anhydride/B-styrene sulfonyl chloride/methacrylic anhydride, glutaric anhydride/ethylene/maleic anhydride copolymer/methacrylic anhydride, glutaric anhydride/polyvinyl sulfonic acid/methacrylic anhydride, glutaric anhydride/ethylene/maleic anhydride copolymer/styrene/maleic anhydride copolymer. Glutaric substitution was important to provide a clear, colorless solution and clear films. Glutaric anhydride could be replaced by succinic anhydride, maleic anhydride or similar anhydrides, sulfonyl chlorides, or acid halide chlorides. Methacrylic substitution provided plastic-like properties and seemed to be associated with spontaneous polymerization. Vinyl substitution appeared to provide plastic-like properties and films that exhibited unusual swelling ability. Styrene substitution appeared to improve the stability of formed films. Ethylene substitution also seemed to enhance the stability of films, although most ethylene films were slightly cloudy.

EXAMPLE 6

Formed Articles

Solutions of substituted soluble collagen were made into lens-like articles by placing aliquots of the solutions in glass molds, 22 mm in diameter by 7 mm in depth. Solutions were then polymerized by UV-irradiation in nitrogen, dried in a laminar-flow hood and then subjected to UV-irradiation, or heated to melt the thick solution, dried, and then subjected to UV-irradiation. Heating seemed to enhance the strength and flexibility of resultant films. Molded films were concave with diameters from 7 mm to 20 mm and thickness form 0.1 mm to 5 mm. Flat films were also prepared by casting the substituted collagen solutions on microscope slides. Thick, lens-shaped films were also prepared by mixing 1-20 milligrams of sodium persulfate into the substituted collagen solutions and then exposing molded material to UV-irradiation for 1-5 minutes, in air. These films were not strong and are easy to tear.

What is claimed is:

1. A biologically compatible collagenous reaction product comprising collagen reacted with an acylating agent selected from the group consisting of glutaric anhydride, succinic anhydride, and maleic anhydride and at least one other acylating agent selected from the group consisting of methacrylic anhydride, beta-styrene sulfonyl chloride, ethylene/maleic anhydride copolymer, styrene/maleic anhydride copolymer, and poly(vinyl) sulfonic acid.

2. A biologically compatible collagenous reaction product according to claim 1 comprising collagen reacted with glutaric anhydride and at least one member of the group consisting of methacrylic anhydride, beta-styrene sulfonyl chloride, ethylene/maleic anhydride copolymer, styrene/maleic anhydride copolymer, and poly(vinyl) sulfonic acid.

3. The collagenous reaction product according to claim 1, wherein said collagen is selected from the group consisting of purified Type I collagen, Type IV collagen, Type III collagen, intact collagen-rich tissue and combinations thereof.

4. The collagenous reaction product according to claim 3, wherein said collagen comprises Type I collagen.

5. The collagenous reaction product according to claim 4, wherein said Type I collagen is derived from bovine tissue.

6. The collagenous reaction product according to claim 4, wherein said Type I collagen is derived from human tissue.

7. A biologically compatible collagenous reaction product comprising collagen reacted with at least one member of the group consisting of methacrylic anhydride, beta-styrene sulfonyl chloride, ethylene/maleic anhydride copolymer, styrene/maleic anhydride copolymer, and poly(vinyl) sulfonic acid.

8. The collagenous reaction product according to claim 7, wherein said collagen is selected from the group consisting of purified Type I collagen, Type IV collagen, Type III collagen, intact collagen-rich tissue and combinations thereof.

9. The collagenous reaction product according to claim 8, wherein said collagen comprises Type I collagen.

10. The collagenous reaction product according to claim 9, wherein said Type I collagen is derived from bovine tissue.

11. The collagenous reaction product according to claim 9, wherein said Type I collagen is derived from human tissue.

12. A polymerized biologically compatible collagenous reaction product useful to form medical implant articles comprising the collagenous reaction product of claim 1.

13. The polymerized reaction product according to claim 12, wherein said collagen is selected from the group consisting of purified Type I collagen, Type IV collagen, Type III collagen, intact collagen-rich tissue and combinations thereof.

14. The polymerized reaction product according to claim 13, wherein said collagen comprises Type I collagen.

15. The polymerized reaction product according to claim 14, wherein said Type I collagen is derived from bovine tissue.

16. The polymerized reaction product according to claim 14, wherein said Type I collagen is derived from human tissue.

17. The polymerized reaction product according to claim 12, wherein said product has been polymerized by exposure to ultraviolet irradiation, chemical agents, atmospheric oxygen or combinations of the foregoing.

18. A polymerized biologically compatible collagenous reaction product useful to form medical implant articles comprising the collagenous reaction product of claim 7.

19. The polymerized reaction product according to claim 18, wherein said collagen is selected from the group consisting of purified Type I collagen, Type IV collagen, Type III collagen, intact collagen-rich tissue and combinations thereof.

20. The polymerized reaction product according to claim 19, wherein said collagen comprises Type I collagen.

21. The polymerized reaction product according to claim 20, wherein said Type I collagen is derived from bovine tissue.

22. The polymerized reaction product according to claim 20, wherein said Type I collagen is derived from human tissue.

23. The polymerized reaction product according to claim 19, wherein said product has been polymerized by exposure to ultraviolet irradiation, chemical agents, atmospheric oxygen or combinations of the foregoing.

* * * * *